US010028913B2

(12) United States Patent
Li et al.

(10) Patent No.: US 10,028,913 B2
(45) Date of Patent: Jul. 24, 2018

(54) LIPOSOMAL PHARMACEUTICAL PREPARATION AND METHOD FOR MANUFACTURING THE SAME

(71) Applicant: CSPC ZHONGQI PHARMACEUTICAL TECHNOLOGY (SHIJIAZHUANG) CO., LTD., Shijiazhuang, Hebei Province (CN)

(72) Inventors: Chunlei Li, Shijiazhuang (CN); Jinxu Wang, Shijiazhuang (CN); Caixia Wang, Shijiazhuang (CN); Yanhui Li, Shijiazhuang (CN); Dongmin Shen, Shijiazhuang (CN); Wenmin Guo, Shijiazhuang (CN); Li Zhang, Shijiazhuang (CN); Lan Zhang, Shijiazhuang (CN)

(73) Assignee: CSPC ZHONGQI PHARMACEUTICAL TECHNOLOGY (SHIJIAZHUANG) CO., LTD, Hebei (CN)

( * ) Notice: Subject to any disclaimer, the term of this patent is extended or adjusted under 35 U.S.C. 154(b) by 0 days.

(21) Appl. No.: 15/138,527

(22) Filed: Apr. 26, 2016

(65) Prior Publication Data
US 2016/0235671 A1 Aug. 18, 2016

Related U.S. Application Data

(62) Division of application No. 12/521,357, filed as application No. PCT/CN2007/071403 on Dec. 29, 2007.

(30) Foreign Application Priority Data

Dec. 29, 2006 (CN) .......................... 2006 1 0102339

(51) Int. Cl.
*A61K 9/127* (2006.01)
*A61K 31/136* (2006.01)
*A61K 31/704* (2006.01)

(52) U.S. Cl.
CPC .......... *A61K 9/1273* (2013.01); *A61K 9/1271* (2013.01); *A61K 31/136* (2013.01); *A61K 31/704* (2013.01)

(58) Field of Classification Search
CPC ..................................................... A61K 9/127
See application file for complete search history.

(56) References Cited

U.S. PATENT DOCUMENTS

| | | |
|---|---|---|
| 5,169,635 A | 12/1992 | Ono et al. |
| 5,356,633 A | 10/1994 | Woodle et al. |
| 5,858,397 A | 1/1999 | Lim et al. |
| 5,939,096 A | 8/1999 | Clerc et al. |
| 6,465,008 B1 | 10/2002 | Slater et al. |
| 6,740,335 B1 | 5/2004 | Moynihan et al. |
| 7,205,299 B2* | 4/2007 | Gerlach ............... C07D 401/12 514/248 |
| 7,288,396 B2* | 10/2007 | Hu ........................ C12N 15/52 435/183 |
| 2002/0102298 A1 | 8/2002 | Needham |
| 2003/0219476 A1 | 11/2003 | Ahmad et al. |
| 2005/0100590 A1 | 5/2005 | Duena et al. |
| 2006/0034906 A1 | 2/2006 | Boni et al. |
| 2006/0222696 A1* | 10/2006 | Okada .................. A61K 9/1271 424/450 |
| 2006/0241076 A1 | 10/2006 | Uhlmann et al. |
| 2007/0065498 A1* | 3/2007 | O'Halloran ............ A61K 9/127 424/450 |
| 2007/0116753 A1 | 5/2007 | Hong et al. |
| 2007/0196461 A1 | 8/2007 | Weers |
| 2014/0044777 A1 | 2/2014 | Kikuchi et al. |

FOREIGN PATENT DOCUMENTS

| | | |
|---|---|---|
| AU | 2007341803 A2 | 7/2008 |
| CN | 1148336 A | 4/1997 |
| CN | 1469735 | 1/2004 |
| CN | 1602844 A | 4/2005 |
| CN | 1242740 C | 2/2006 |
| EP | 0912198 B1 | 6/2006 |
| ES | 2186484 B1 | 5/2003 |
| JP | 2003510239 A | 3/2003 |
| JP | 2006508126 A | 3/2006 |
| JP | 2006515578 A | 6/2006 |
| JP | 2006298844 A | 11/2006 |
| JP | 2009543335 A | 12/2009 |
| RU | 22558530 C1 | 8/2005 |

(Continued)

OTHER PUBLICATIONS

Zhu, G., et al in Cancer Chemother Pharmacol. vol. 39, pp. 138-142, 1996.*
Adams, David J., "The Impact of Tumor Physiology on Camptothecin-Based Drug Development", Curr. Med. Chem.—Anti-Cancer Agents, 2005, 5, pp. 1-13.
European Search Report EP07846229; Dated Feb. 8, 2010.
George Zhu et al., The effect of vincristine-polyanion complexes in STEALTH liposomes on pharmacokinetics, toxicity and anti tumor activity, Aug. 28, 1995, Cancer Chemother Pharmacol (1996) 39, p. 138-142.
International Search Report corresponding to Application No. PCT/CN2007/071403; Dated Apr. 10, 2008.
James, E. Trosko, Chia-Cheng Chang, "mechanism of up-regulated gap junctional intercellular communication during chemo-prevention and chemotherapy of cancer", Mutation Research 480-481 (2001) 219-229.

(Continued)

*Primary Examiner* — Gollamudi Kishore
(74) *Attorney, Agent, or Firm* — Seed IP Law Group LLP

(57) ABSTRACT

The present invention relates to a liposomal pharmaceutical preparation containing a multivalent ionic drug, a process for the preparation of the liposomal pharmaceutical preparation, and a use thereof in the treatment of diseases, in which the liposome has a size of about 30-80 nm, and the phospholipid bilayer has a phospholipid with a Tm higher than body temperature, so that the phase transition temperature of the liposome is higher than the body temperature.

13 Claims, 3 Drawing Sheets

(56) References Cited

FOREIGN PATENT DOCUMENTS

| WO | 9713499 | A1 | | 4/1997 |
|---|---|---|---|---|
| WO | 0105372 | A2 | | 1/2001 |
| WO | 2004043363 | A2 | | 5/2004 |
| WO | 2004/047800 | | * | 6/2004 |
| WO | 2004093795 | A2 | | 11/2004 |

OTHER PUBLICATIONS

Lu Wanliang, "Development of the stealth doxorubicin in liposomes and tissue distribution in mice", Journal of Chinese Pharmacy, May 1999, vol. 34, No. 5, pp. 310-312.
Modified Substantive Examination Adverse Report for Malaysian Application No. PI20092715, dated Mar. 29, 2013.
N. Berger et at, "Filter extrusion of liposomes using different devices: comparison of liposome size, encapsulation efficiency, and process characteristics", International Journal of Pharmaceutics 223 (2001) p. 55-68.
Office Action for Japanese Patent Application No. 2009-543335, dated Jun. 12, 2012, with English translation.
Office Action for the Japanese Patent Application No. 2013-082307, dated Mar. 18, 2014. English translation attached.
Russian 1st Office Action for Russian patent application No. 2009126983/15(037542) dated Oct. 19, 2011 with English translation.
Second Office Action for Russian Application No. 2009126983/15 (037542), dated Jun. 20, 2012, with English translation.
Summons to attend oral proceedings pursuant to Rule 115(1) EPC; dated Dec. 13, 2011.
U.S. Final Office Action corresponding to U.S. Appl. No. 12/521,357; dated May 2, 2012.
U.S. Final Office Action corresponding to U.S. Appl. No. 12/521,357; dated Oct. 10, 2014.
U.S. Final Office Action corresponding to U.S. Appl. No. 12/521,357; dated Oct. 26, 2015.
U.S. Non Final Office Action corresponding to U.S. Appl. No. 12/521,357; dated Apr. 17, 2015.
U.S. Non Final Office Action corresponding to U.S. Appl. No. 12/521,357; dated Dec. 19, 2011.
U.S. Non Final Office Action corresponding to U.S. Appl. No. 12/521,357; dated Jun. 27, 2014.
Yi-Song Duan, et al., "Study on the Preparation Techniques of Mitoxantrone Liposomes" China Academic Journal Electronic Publishing House, 2001, vol. 16 (2), pp. 91-92.
Yi-Song Duan, et al.; "Preparation of Long Circulating Mitoxantrone Liposomes and Its Pharmacokinetics", Acta Pharmaceutica Sinica, 2002, 37(6) pp. 465-468.
Yuan Huang, et al. "Studies on preparation of long circulating mitozantrone liposomes with transmembrane ammonium sulfate gradients", China Academic Journal Electronic Publishing House, 2002, vol. 37 No. 12, pp. 917-919.
U.S. Final Office Action corresponding to U.S. Appl. No. 12/521,357; dated Oct. 17, 2016.
Decision of Final Rejection dated Jan. 31, 2017, for corresponding Japanese Application No. 2015-096518 (with English translation) (14 pages).
Suzuki, "Aiming for cancer treatment using liposome technology," *Pharmaceuticals* 68(4):252-257, with English translation (16 pages) (2008).

* cited by examiner

LIPOSOMAL PHARMACEUTICAL PREPARATION AND METHOD FOR MANUFACTURING THE SAME

The present application is a divisional application of U.S. patent application Ser. No. 12/521,357, filed on Jun. 26, 2009, the entire contents of which are incorporated herein by reference and priority to which is hereby claimed. Application Ser. No. 12/521,357 is the U.S. National stage of application No. PCT/CN2007/071403, filed Dec. 29, 2007. Priority under 35 U.S.C. § 119(a) and 35 U.S.C. § 365(b) is hereby claimed from Chinese Application No. 200610102339.8, filed Dec. 29, 2006, the disclosure of which is also incorporated herein by reference.

FIELD OF INVENTION

The present invention relates to a liposomal preparation and a drug-encapsulating liposomal pharmaceutical preparation, especially to a liposomal pharmaceutical preparation of mitoxantrone. The present invention further relates to methods for manufacturing the liposome, liposomal pharmaceutical preparation and uses thereof.

BACKGROUND OF THE INVENTION

Liposomes can be used as a carrier for many drugs, especially for antitumor drugs (in particular chemotherapeutic drugs). Liposomes can reduce the distribution of drug in normal tissues, but increase the accumulation of drug in tumor tissues, thereby improving the therapeutic index of drug. The reason why a liposome can target passively to a tumor relates to the physiological properties of tumor tissue. Tumor blood vessels may have a pore size of up to 100-780 nm due to its rapid growth, while normal vascular endothelial cells have a typical space of about 2 nm. Therefore, liposomes can accumulate passively in tumor region if they can circulate for a relatively long period in blood and have a size of less than 200 nm, because after liposomes with small size are administered via intravenous injection, they can not enter normal tissues but can penetrate blood vessel of tumor region and arrive at treatment area.

However, it is not easy to achieve the therapeutic advantages of liposome, and the following four requirements have to be met: (1) the drug can be encapsulated in liposome in a good encapsulation efficiency and a sufficient drug loading; (2) the drug will not be released from the liposome during storage period in vitro; (3) there is not a notable drug leakage during blood circulation of liposomal drug; and (4) the drug can be released effectively and thereby exerting its therapeutic effects when liposomes are accumulated in the tumor region. With regard to the current liposome techniques, the former three problems have been solved well, therefore, the rational release in vivo of liposomal drug draws more attentions. One critical technical problem to be solved for developing some liposomal drugs is to effectively control the rational release of liposomal drugs after targeting to a tumor region. This is especially important for some drugs, such as mitoxantrone.

It was found by a liposome study group in Canada that a liposome formulation having a size of about 100 nm, which was prepared by using hydrogenated soybean phosphatidylcholine (HSPC) and cholesterol as phospholipid bilayer and loading drug by a 300 mM citric acid gradient, was not as good as free mitoxantrone. In order to improve the therapeutic effect of liposome, the group finally changed the composition of phospholipid bilayer into dimyristoyl phosphatidylcholine (DMPC) and cholesterol, and obtained a preparation with improved therapeutic indexes. However, the leakage of drug may increase during the storage period because the phase transition temperature of DMPC is about 21° C., so that the preparation may not be stable (Liposomal formulations of mitoxantrone, U.S. Pat. No. 5,858,397).

Neopharm Corporation of USA used another technique to develop a liposome formulation of mitoxantrone, in which a cardiolipin carrying negative charge was added to phospholipid bilayer. Due to the intensive interaction between cardiolipin and mitoxantrone, mitoxantrone could be inserted into the phospholipid bilayer in a passive loading mode. This passive loading technique is different from active loading technique. By virtue of active loading technique, a drug would deposit in the intraliposomal aqueous phase in a form of precipitation. The Phase I clinical study on the product of Neopharm indicated that liposome drugs could increase the possibility of occasional infection, compared with free drug. The development of this product was ceased in view of safety (Liposomal preparations of mitoxantrone, CN01817424.8).

Pacific Institute of Materia Medica (Changchou, China) also filed a patent application for a liposomal preparation of mitoxantrone (A liposomal injection of mitoxantrone or mitoxantrone hydrochloride and the process for making the same, CN200410041612.1). In this application, traditional pH value gradient method was used to load drugs. This application seeks to protect a formulation with a specific ratio, and does not disclose the effects of factors such as composition of phospholipids, kinds of buffer salts in internal aqueous phase, size of liposome, drug/liposome ratio, etc. on the therapeutic efficacy and toxicity of liposome.

Zhirong Zhang, et al of West China School of Pharmacy, Sichuan University also studied liposomal preparations of mitoxantrone. They used soybean phosphatidylcholine with a phase transition temperature of 0° C. (which is marketed under the trade name EPIKURON 200) to prepare liposomes of about 60 nm. In this article, only pharmacokinetics was studied without concerning toxicity and therapeutic efficacy of the obtained liposomal preparation. Relevant contents can be seen in "Preparation of long circulating mitoxantrone liposomes and its pharmacokinetics", Zhirong Zhang, Botao Yu and Yisong Duan, Acta Pharmaceutica Sinica, 2002, Vol. 37, No. 6; Studies on preparation of long circulating mitoxantrone liposomes with transmembrane ammonium sulfate gradients, Zhirong Zhang, Botao Yu, Yisong Duan and Yuan Huang, Chinese Pharmaceutical Journal, 2002 Vol. 37, No. 12; and Study on the preparation techniques of mitoxantrone liposomes, Yisong Duan, West China Journal of Pharmaceutical Sciences, 2001 Vol. 16, No. 02.

In the above studies, the size of liposomes is usually controlled in the range of 80~150 nm, since there is a consensus in the field of liposome that a liposome with a size of about 100 nm would have the best targeting efficiency (Pharmacol. Rev. 1999 51: 691-744.). However, as mentioned above, a liposome should not only have an excellent targeting efficiency, but also a sufficient release from liposome to exert its effect.

As indicated above, according to the prior field, the leakage of drug during blood circulation should be essentially avoid so that the drug could be effectively transferred to tumors, but this requirement also results in a difficulty of releasing the drug from the liposome when it is targeted to tumor region. In conventional processes for making liposomes, a drug is usually encapsulated by a active loading technique, in which the drug encapsulated in the liposome is present in a colloid precipitate form having no bioactivity, so that only when the drug is released effectively from the liposome, it can change into a therapeutic drug with bioactivity. If the release rate of drug is too slow, the drug can hardly exert its therapeutic actions even though it has been targeted effectively to the tumor region, and its therapeutic effect may be even inferior to an unencapsulated drug.

Therefore, there is an urgent need in the field for a liposomal preparation capable of delivering a drug with good targeting ability and releasing the drug in the targeted tissues effectively, and for a corresponding liposomal pharmaceutical preparation.

SUMMARY OF THE INVENTION

The present inventors surprisingly found by chance that some drugs having a plurality of dissociable groups and a liability of forming compact precipitate with multivalent counter ion, could be processed to form a small unilamellar liposomal preparation with an effectively improved therapeutic index, so that the above technical problem could be solved.

Therefore, in one aspect, the present invention provides a liposomal preparation with a size of about 30-80 nm having a phospholipid with a Tm higher than body temperature in phospholipid bilayer, so that the phase transition temperature of liposome is higher than the body temperature. Examples of said phospholipid include but are not limited to phosphatidylcholine, hydrogenated soybean phosphatidylcholine (HSPC), hydrogenated egg-yolk phosphatidylcholine, dipalmitoyl phosphatidylcholine (DPPC) or distearoyl phosphatidylcholine (DSPC) or any combination thereof.

In one embodiment, the phospholipid with a Tm higher than body temperature in the phospholipid bilayer represents 50-100 mol/mol %, preferably 55-95 mol/mol %, and more preferably 55-95 mol/mol % of the total content of phospholipids.

Optionally, the phospholipid bilayer of the liposomal preparation of the present invention further comprises additional phospholipids, for example, a phospholipid with a Tm not higher than the body temperature, such as dimyristoyl phosphatidylcholine (DMPC) and the like. The amount of the phospholipid in the liposomal preparations of the present invention can be conventionally determined by those of ordinary skilled in the field, provided that the Tm value of the liposomal preparation is not markedly reduced to a value lower than the body temperature.

The liposomal preparation of the present invention can also optionally comprise cholesterol in order to regulate the fluidity of liposome membrane.

The liposomal preparation of the present invention can also optionally comprise additional excipients, especially excipients for further modifying surface characteristics of liposome to confer the liposome better behavior in vivo. Such excipients include, for example, lipids and the like modified with hydrophilic polymers.

In another aspect, the present invention provides a liposomal pharmaceutical preparation, which comprises a drug of interest, especially a multivalent ionic drug, in a liposomal preparation of the present invention. Therefore, the present invention relates to a liposomal pharmaceutical preparation having a size of 30-80 nm, wherein: (1) the liposomal pharmaceutical preparation comprises a multivalent ionic drug as active ingredient; (2) the phospholipid bilayer comprises a phospholipid with a Tm higher than body temperature so that the phase transition temperature of the liposome is higher than the body temperature; and optionally (3) the liposomal pharmaceutical preparation comprises additional drugs and/or additional excipients acceptable in the liposomal pharmaceutical preparation. Preferably, the main peaks of size of the liposomal pharmaceutical preparation are centered around 35-75 nm, especially around 40-60 nm.

In another aspect, the present invention provides a method for preparing the above liposomal pharmaceutical preparation, the method comprising the following steps: (1) preparing a liposome using a phospholipid with a Tm higher than body temperature and optionally additional phospholipids and/or cholesterol; and (2) encapsulating a drug of interest, especially a multivalent ionic drug in the liposome.

The present invention also provides a method for treatment of disease, comprising administering a liposomal pharmaceutical preparation of the present invention to a subject in need of the treatment. Preferably, the subject is a mammal, especially a human being.

DESCRIPTION OF THE PREFERRED EMBODIMENTS

Figure 1:
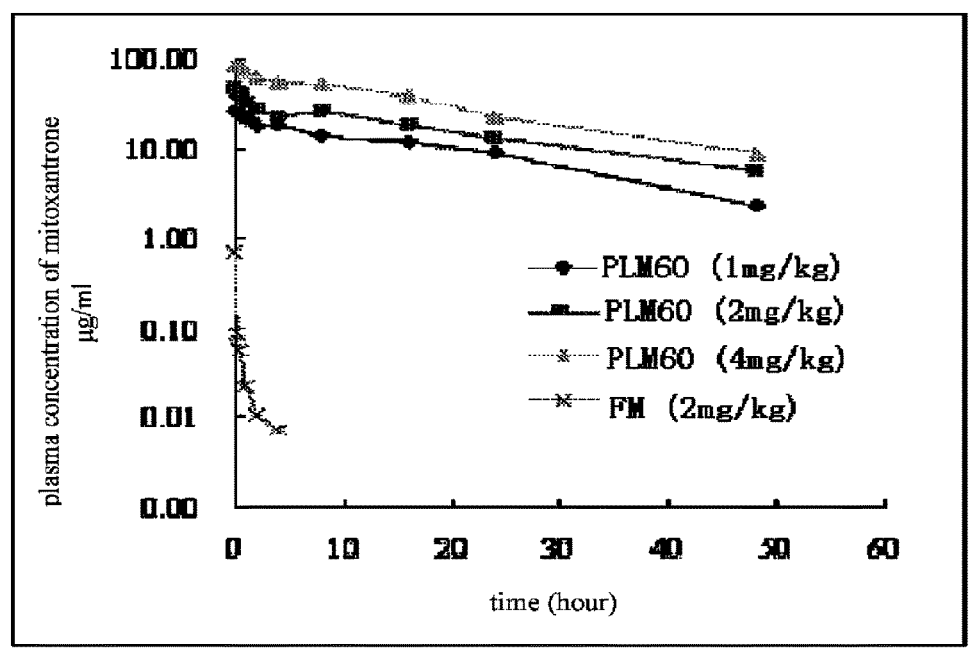
FIG. 1 is the in vivo pharmacokinetics of PLM60 in Kunming mice and the comparison thereof with the in vivo pharmacokinetics of free mitoxantrone, in which PLM represents PEGylated mitoxantrone liposome, FM represents free mitoxantrone, the abscissa represents time (hour) and the ordinate represents plasma level of mitoxantrone (μg mitoxantrone/mL plasma).

Usually, liposomes are formed with phospholipids and cholesterol as membrane materials. These two ingredients not only are the basic materials for forming liposome bilayer, but also have very important physiological functions.

The physical properties of liposomal membrane are closely related to the temperature. When temperature is elevated, acyl side chains of lipid bilayer change form ordered array into unordered array. This kind of change can result in many changes of physical properties of lipid membrane. For example, "gel" state may change into "liquid crystal" state, the cross section of membrane may increase, the thickness of bilayer may decrease, the membrane fluidity may increase. The temperature at which such changes happen is called phase transition temperature. The phase transition temperature of lipid membrane can be determined by Differential Scanning Calorimertry, Electron Spins Resonance (ESR) and the like. The phase transition temperature of liposome membrane depends on the kinds of phospholipids. Generally, the longer the acyl side chain, the higher the phase transition temperature; and vice versa. For example, the phase transition temperature of dimyristoyl phosphatidylcholine is 24° C., while those of dipalmitoyl phosphatidylcholine and distearoyl phosphatidylcholine are 41° C. and 58° C., respectively. Membrane fluidity is an important property of liposome. At phase transition temperature, membrane fluidity will increase, and the drug encapsulated in the liposome has the maximum release rate. Thus the membrane fluidity affects directly the stability of liposome.

In one embodiment, the present invention provides a liposome preparation having a size of about 30-80 nm and a phospholipid with a Tm higher than body temperature in phospholipid bilayer, so that the phase transition temperature of liposome is higher than the body temperature.

Preferably, the liposomal pharmaceutical preparation of the present invention is prepared by using phospholipids with a relatively high phase transition temperature Tm, such as phosphatidylcholine. If the Tm of phosphatidylcholine is higher than the body temperature, the length of its hydrocarbon chain is preferably not less than 16 carbons. Preferably, the phospholipids of the present invention include but not limited to hydrogenated soybean phosphatidylcholine, hydrogenated egg-yolk phosphatidylcholine, dipalmitoyl phosphatidylcholine (DPPC) or distearoyl phosphatidylcholine (DSPC), or any combination thereof.

In the liposomal preparation of the present invention, the phospholipids with a Tm higher than the body temperature in phospholipid bilayer represent about 50-100 mol/mol %, preferably about 55-95 mol/mol %, more preferably about 60-90 mol/mol % relative to the total content of all phospholipids. Optionally, the phospholipid bilayer may comprise additional phospholipids, for example, phospholipids with a Tm not higher than the body temperature, such as dimyristoyl phosphatidylcholine (DMPC) and the like. Such phospholipids may be present in the liposome in any suitable amount, provided that it does not render the phase transition temperature of the liposomal preparation below the body temperature. The suitable amount can be determined according to conventional techniques by those of ordinary skilled in the field.

Preferably, the liposomal preparation of the present invention may further comprise cholesterol. Cholesterol has a function of regulating membrane fluidity. When the liposome membrane comprises 50% (mol/mol) cholesterol, the phase transition of liposome membrane may disappear. Cholesterol is called "fluidity buffer" by Papahadjopoulos et al., because the addition of cholesterol to phospholipids under phase transition temperature can reduce the ordered array of membrane and increase membrane fluidity, while the addition of cholesterol to phospholipids above the phase transition temperature can increase the ordered array of membrane and reduce the membrane fluidity. In the liposomal preparation of the present invention, the content of cholesterol can be 2-60 mol/mol %, 5-55 mol/mol % or 10-50 mol/mol % relative to the total amount of ingredients of liposome. More specifically, the content of cholesterol can be 15-45 mol/mol %, for example 20-40 mol/mol % relative to the total amount of ingredients of liposome. The content of cholesterol in the liposome of the present invention can be determined easily according to conventional techniques by those of ordinary skilled in the field.

It should be appreciated that the phospholipid bilayer in the liposome of the present invention can also comprise additional excipients, especially excipients for further modifying surface characteristics of the liposome to confer better in vivo behaviors to the liposome. Such excipients include, for example, lipid substances modified with hydrophilic polymers, and the examples thereof are PEG-modified distearoyl phosphatidyl ethanolamine (DSPE-PEG), PEG-modified distearoyl phosphatidyl glycerol (DSPG-PEG), PEG-modified cholesterol (chol-PEG), polyvidone-modified distearoyl phosphatidyl ethanolamine (DSPE-PVP), polyvidone-modified disteroyl phosphatidyl glycerol (DSPG-PVP), or polyvidone-modified cholesterol (chol-PVP). Said excipients can also be membrane materials modified with a specific antibody or ligand. The amount of such excipients in the liposome of the present invention can be determined according to conventional techniques by those of ordinary skilled in the field, for example, can be 0.1-20 mol/mol %, preferably 0.3-18 mol/mol %, more preferably 0.5-15 mol/mol %, especially 0.8-12 mol/mol %, for example 1-10 mol/mol %, or 2-8 mol/mol %, 2.5-7 mol/mol %, 3-6 mol/mol %, etc. relative to the mole number of phospholipids. In the cases of using PEG-modified lipids as excipients, the molecular weight of PEG moiety can be, for example, 400-20000 Dalton, preferably 600-15000 Dalton, more preferably 800-10000 Dalton, especially 1000-8000 Dalton, for example 1200-5000 Dalton. The use of PEG in the present invention can also be determined easily according to conventional trails by those of ordinary skilled in the field.

The liposomal preparation of the present invention is a small unilamellar liposomal preparation, and should have a suitable size. Preferably, the size of the preparation is 30-80 nm, more preferably 35-70 nm, especially preferably 40-60 nm. The size of liposome can be determined by particle size analyzer or electron microscope or other means. It should be understood that the liposome particles in the present invention can not have a completely uniform size, but span a size range, due to the nature of liposome per se and properties of manufacture process. Therefore, in the liposomal preparation of the present invention, the presence of liposome particles out of the stated size range may not be excluded, provided that they do not evidently affect the characters of the liposomal preparation or pharmaceutical preparation of the present invention.

The liposome in the present invention can be prepared by various suitable methods, including, for example, film dispersion method, injection method, ultrasonic dispersion method, freeze-drying method, freeze-thaw method and the like. According to the starting systems used for preparing liposome, the methods can be divided into: (1) methods based on dry lipid membrane, lipid powder; (2) methods based on emulsifying agents; (3) liposome preparation methods based on mixed micelles; and (4) liposome preparation methods based on a triple phase mixture of ethanol, phospholipids and water. The encapsulation of drug can be implemented by either passive loading mode or active loading mode. These methods can be found in many review articles about liposomes.

During or after the preparation of liposomal preparation, many suitable methods can be used to encapsulate a drug in liposome and form a liposomal pharmaceutical preparation. Suitable methods include for example active loading methods and passive loading methods. Active loading method is usually performed by gradient methods, for example an ammonium sulfate gradient method, i.e., using an ammonium sulfate solution as aqueous phase to firstly prepare a liposome comprising ammonium sulfate in both intraliposomal and extraliposomal phase, then forming a concentration gradient of ammonium sulfate between the intraliposomal and extraliposomal phase by removing extraliposomal ammonium sulfate. Intraliposomal NH4+ dissociates into NH3 and H+, which leads to a concentration difference of H+ (i.e. pH gradient) between intraliposomal and extraliposomal phase, so that after an extraliposomal drug in molecular state enters into the intraliposomal aqueous phase, it changes into ionic state, thereby the drug can not return to the extraliposomal aqueous phase and the liposome has less leakage of drug and is more stable. Passive loading method can be performed by organic solvent injection method, film dispersion method, freeze-thaw method, and the like.

In the present invention, any suitable drug ingredients can be used. Preferably, the active pharmaceutical ingredient in the liposomal pharmaceutical preparation of the present invention is a multivalent ionic drug. The term "multivalent ionic drug" means a drug having two or more dissociable groups with a dissociation constant pKa of 4.5~9.5, so that the drug has more positive charges or more negative charges in the ranges of pKa. Preferably, said dissociation constant is in the range of 5.0-9.5. More preferably, said dissociation constant is in the range of 5.5-9.5. Especially preferably, said dissociation constant is in the range of 6.0-9.0 m, especially 6.5-9.0. The pKa value of each dissociable group of ion drug can be determined easily according conventionally techniques by those of ordinary skilled in the field.

In the present invention, the multivalent ionic drugs can include but are not limited to anticancer drugs, for example, drugs useful for prevention or treatment of the following cancers: lung cancers (such as non-small cell lung cancer), pancreas cancer, breast cancer, rectum cancer or multiple myeloma, liver cancer, cervical carcinoma, gastric carcinoma, carcinoma of prostate, renal carcinoma and/or carcinoma of bladder. Therefore, in one embodiment of the present invention, the multivalent ionic drug is a multivalent ion anticancer drug. Preferably, the multivalent ionic drug is mitoxantrone, vincristine, vinorelbine or vinblastine. More preferably, said multivalent ionic drug is mitoxantrone and can optionally combine with at least one of additional drugs, which can for example be an antitumor drug, such as vincristine, vinorelbine or vinblastine, and the like.

It is necessary to specifically note that in the prevent invention, the multivalent ionic drug can also be a combination of any one or two or more of the above drugs, for example, a combination of two anticancer drugs, a combination of one or more anticancer drugs with additional drugs such as immunopotentiator, and a combination of two or more other kinds of drugs.

It should also be noted that the liposomal drugs of the present invention can also optionally comprise one or more of additional non-multivalent ionic drugs besides the multivalent ionic drugs mentioned above, which can be administered in combination with the multivalent ionic drugs as mentioned above. The combinatory administration comprises the administration with all the components in one preparation, also comprises the combinatory administration in separate unit dosage form.

It should be appreciated that the drug as active ingredient as mentioned herein comprises not only its original form, but also its derivatives, for example solvates (such as hydrates and alcohol addition products), prodrugs and other physiologically acceptable derivatives, as well as active metabolites, and the like. Derivatives, prodrugs and other physiologically acceptable derivatives as well as active metabolites of a drug are all well known to those of ordinary skilled in the field.

The liposomal pharmaceutical preparation of the present invention can further comprise two or more multivalent counter ions with charges opposite to that of active ingredient. Examples of the multivalent counter ions include but are not limited to organic acid anions, such as acid anions of the following saturated or unsaturated organic acids: citric acid, tartaric acid, fumaric acid, oxalic acid, malonic acid, succinic acid, malic acid and maleic acid, and the like; inorganic acid anions, such as sulfate anion, phosphate anion and the like. Among them citrate anion, sulfate anion or phosphate anion are preferred. Furthermore, said multivalent counter ions can also be amino acids, such as cystine and the like. Without being bound by any specific theory, it is presumed that the multivalent counter ion is able to form an insoluble precipitate with a drug of interest (e.g., multivalent ionic drug) encapsulated in the liposome, thereby the existence of the multivalent ionic drug in the liposome is stabilized.

The liposomal pharmaceutical preparation of the present invention further comprises optionally additional excipients and carriers commonly known in the pharmaceutical field, such as sucrose, histidine, antioxidants, stabilizers, dispersants, preservatives, diluents, solvents, salts for altering osmotic pressure, and the like.

In one embodiment, the present invention provides a method for preparing the liposomal pharmaceutical preparation of the present invention, comprising: firstly preparing the liposomal preparation of the present invention as mentioned above, and subsequently incubating a drug of interest with the liposomal preparation in a suitable condition. More specifically, the method for preparing the liposomal pharmaceutical preparation of the present invention comprises the following steps: (1) dissolving lipid excipients suitable for preparing a liposome in a suitable organic solvent, such as tert-butyl alcohol or cyclohexane, then lyophilizing to obtain a lyophilized powder; (2) hydrating the lyophilized powder with a solution containing a counter ion of the drug active ingredient of interest to form an empty liposome; (3) removing the extraliposomal counter ion by a suitable means such as dialysis or column chromatography and the like in order to form a counter ion gradient between the intraliposomal phase and extraliposomal phase; and (4) incubating the drug with the liposome to obtain the liposome drug. Descriptions about phospholipids, cholesterol, excipients and the like refer to the supra for the liposomal preparation.

Preferably, the lipid is a phospholipid, especially a lipid with a relatively high phase transition temperature, for example, phosphatidylcholine, hydrogenated soybean phosphatidylcholine, hydrogenated egg yolk phosphatidylcholine, dipalmitoyl phosphatidylcholine (DPPC) or distearoyl phosphatidylcholine (DSPC), or any combination thereof. Optionally, said lipid can also comprise cholesterol in an amount of, for example, 2-60 mol/mol %, 5-55 mol/mol % or 10-50 mol/mol %. More specifically, the amount of cholesterol can be 15-45 mol/mol %, for example 20-40 mol/mol % relative to the total mole number of all ingredients in the liposome. Those of ordinary skilled in the field can determine the cholesterol amount depending on specific requirements for the phase transition temperature of liposome to be obtained and the desired properties.

Once the liposomal pharmaceutical preparation is prepared, the encapsulation efficiency of drug in liposome can be determined by conventional techniques. Methods for determining the encapsulation efficiency of liposome includes ultrafiltration, dialysis, column chromatography, minicolumn centrifugation, and the like. Ultrafiltration is not used due to the high requirements for experiment device; column chromatography is not used because the dilution requires a large amount of eluent, and the content of drug is very low, so that it is difficult to conduct content determination, moreover, the dilution of a large amount of eluent can also lead to leakage of drug in liposome, it can be known from trial data that the encapsulation efficiency for dialysis is lower (perhaps due to the breakage of liposome after dilution) and the time for dialysis is long, thus the method is not suitable. Determination of encapsulation efficiency by minicolumn centrifugation has the following advantages: short time consuming, small dilution rate for solution of liposome, and no need for expensive instruments.

The liposomal pharmaceutical preparation of the present invention ensures not only sufficient encapsulation efficiency and sufficient drug loading, but also no release of drug from liposome during in vitro storage, no notable leakage of drug from liposome during blood circulation to increase toxicity. An important notable effect of the liposome drug of the present invention is that the release rate of drug is accelerated efficiently, the therapy index of liposome is improved, the half-life period is significantly prolonged, the toxicity is reduced markedly in comparison with the current products in the field, and thus the effective therapeutic effects of drug are achieved. For example, for a liposomal pharmaceutical preparation prepared by using hydrogenated soybean phosphatidylcholine (HSPC) and dipalmitoyl phosphatidylcholine (DPPC), the toxicity thereof is markedly reduced and the therapeutic index thereof is significantly improved. On the contrary, if the phospholipid bilayer is composed of dimyristoyl phosphatidylcholine (DMPC), the release of drug will be too fast and lead to a notable toxicity, even the safety will not be as good as a free drug. Without being bound by a certain theory, it is presumed that the small unilamellar liposomal preparation of the present invention can accelerate the release of drug because the small unilamellar liposomal preparation may contain more liposome particles in which drug precipitation with a small particle size is contained, in comparison with a larger unilamellar liposome preparation, if the drug/lipid ratio is fixed. Drug precipitation with a small particle size would have a relatively great specific surface area, and thus have a more rapid dissolution rate under same conditions.

Moreover, the liposomal pharmaceutical preparation of the present invention should be prepared using suitable phospholipids in order to achieve an effective release of drug in target tissues, especially in tumors. Preferably, the phospholipid bilayer of the liposomal pharmaceutical preparation of the present invention is composed of phospholipids with a relatively high phase transition temperature. During experiments, it was found that the toxicity of preparation would decrease significantly and the therapeutic index would be improved notably if hydrogenated soybean phosphatidylcholine (HSPC) and dipalmitoyl phosphatidylcholine (DPPC) or the like were employed in the preparation. If the phospholipid bilayer is composed of dimyristoyl phosphatidylcholine (DMPC), the release of drug would be too fast and would lead to a notable toxicity, even the safety would not be as good as an unencapsulated drug.

The liposomal pharmaceutical preparation of the present invention can be administered to a patient in need thereof in an administration route commonly used in the field. In one embodiment of the present invention, the liposome drug is formulated into a preparation for parenteral administration. In one preferred embodiment of the present invention, the liposome drug is administered by injection.

The present invention also provides a method for the treatment of disease, especially tumors in a patient, the method comprising administering a liposomal pharmaceutical preparation of the present invention to the patient in need of the treatment. Preferably, a thermotherapy method (such as a radioactive thermotherapy method) can also be applied in combination to a tumor patient in order to enhance the therapeutic effect of the liposomal pharmaceutical preparation. In the present invention, the patient can be a mammal, preferably a human.

The present invention also relates to a use of the liposomal preparation or liposomal pharmaceutical preparation as mentioned above in the manufacture of a medicament for treatment of a tumor patient.

The present invention is further illustrated by the following examples, which is only exemplary and should not be construed as a limitation to the present invention.

Part 1: Preparation of Liposomes

Example 1

General Methods for Preparing Liposomes

1. General Method 1

Phospholipid (e.g., hydrogenated soy phosphatidylcholine (HSPC), dipalmitoyl phosphatidylcholine (DPPC) or dimyristoyl phosphatidylcholine (DMPC)) and cholesterol (molar ratio of 1:1 to 10:1) are dissolved in an organic solvent, such as t-butyl alcohol or cyclohexane, to form a clear solution. The solution is treated by conventional lyophilization to obtain a lyophilized powder. The lyophilized powder is hydrated at 60-65° C. with (50-1000 mM) ammonium sulfate solution, citric acid solution or transition metal sulfate (e.g., nickel sulfate) solution, and shaken for about 1 hour to obtain heterogenous multilamellar vesicles. The size of the obtained vesicles is reduced by a microfluidizer or a high pressure extrusion apparatus to obtain liposomes. A sample of the obtained liposomes is diluted by 200 times with 0.9% NaCl solution and detected by NanoZS. The extraliposomal buffer solution is removed by ultrafiltration apparatus to form a dynamic transmembrane gradient. A mitoxantrone hydrochloride solution (10 mg/mL) is added to the empty liposomes at a suitable liposome/drug ratio, and the loading of drug is conducted at 60-65° C. After incubation for about 1 hour, a gel exclusion chromatography is employed to determine encapsulation efficiency (EE).

2. General Method 2

Phospholipid (e.g., hydrogenated soy phosphatidylcholine (HSPC), dipalmitoyl phosphatidylcholine (DPPC) or dimyristoyl phosphatidylcholine (DMPC)) and cholesterol (molar ratio of 1:1 to 10:1) are mixed, and a polyethylene glycol-modified distearoyl phosphatidylethanolamine (DSPE-PEG) in 0.1-20% by mole of phospholipid is added at the same time. The obtained mixture is dissolved in an organic solvent, such as t-butyl alcohol or cyclohexane, to form a clear solution. The solution is treated by conventional lyophilization to obtain a lyophilized powder. The lyophilized powder is hydrated at 60-65° C. with (50-1000 mM) ammonium sulfate solution, citric acid solution or transition metal sulfate (e.g., nickel sulfate) solution and shaken for about 1 hour to obtain heterogenous multilamellar vesicles. The size of the obtained vesicles is reduced by a microfluidizer or a high pressure extrusion apparatus to obtain liposomes. A sample of the obtained liposomes is diluted by 200 times with 0.9% NaCl solution and detected by NanoZS. The extraliposomal buffer solution is removed by ultrafiltration apparatus to form a dynamic transmembrane gradient. A mitoxantrone hydrochloride solution (10 mg/mL) is added to the empty liposomes at a suitable liposome/drug ratio, and the loading of drug is conducted at 60-65° C. After incubation for about 1 hour, a gel exclusion chromatography is employed to determine encapsulation efficiency (EE).

Example 2

Preparation of Mitoxantrone Liposome PLM60

HSPC, cholesterol and DSPE-PEG2000 at a weight ratio of 3:1:1 were dissolved in 95% t-butyl alcohol to form a clear solution. The solution was treated by lyophilization to obtain a lyophilized powder. The lyophilized powder was hydrated with an ammonium sulfate solution (300 mM) at 60-65° C. and shaken for about 1 hour to obtain heterogenous multilamellar vesicles having a final concentration of phospholipid of 96 mg/mL. The size of vesicles was reduced by a microfluidizer to obtain liposomes. A sample of the obtained liposomes was diluted by 200 times with 0.9% NaCl and detected by NanoZS, having an average size of about 60 nm and a main peak between 40 nm and 60 nm. The extraliposomal ammonium sulfate solution was removed by an ultrafiltration apparatus and substituted by a solution with 250 mM sucrose and 50 mM glycine to form a dynamic transmembrane gradient. A mitoxatrone hydrochloride solution (10 mg/mL) was added to the empty liposomes at a liposome/drug ratio of 16:1, and the loading of drug was conducted at 60-65° C. After incubation for about 1 hour, the encapsulation efficiency (EE) was determined as 100% by a gel exclusion chromatography. The obtained liposomes were named as PLM60.

Example 3

Preparation of Mitoxantrone Liposome PLM85

HSPC, cholesterol and DSPE-PEG2000 at a weight ratio of 3:1:1 were dissolved in 95% t-butyl alcohol to form a clear solution. The solution was treated by lyophilization to obtain a lyophilized powder. The lyophilized powder was hydrated with an ammonium sulfate solution (300 mM) at 60-65° C. and shaken for about 1 hour to obtain heterogenous multilamellar vesicles having a final concentration of phospholipid of 96 mg/mL. The size of vesicles was reduced by a high pressure extrusion apparatus to obtain liposomes. A sample of the obtained liposomes was diluted by 200 times with NaCl solution and detected by NanoZS, having an average size of about 85 nm. The extraliposomal ammonium sulfate solution was removed by an ultrafiltration apparatus and substituted by a solution with 250 mM sucrose and 50 mM glycine to form a dynamic transmembrane gradient. A mitoxatrone hydrochloride solution (10 mg/mL) was added to the empty liposomes at a liposome/drug ratio of 16:1, and the loading of drug was conducted at 60-65° C. After incubation for about 1 hour, the encapsulation efficiency (EE) was determined as 100% by a gel exclusion chromatography. The obtained liposomes were named as PLM85.

Example 4

Preparation of Mitoxantrone Liposome PLM100

The same method as described in Example 3 was used to prepare mitoxatrone hydrochloride liposome PLM100, in which the formulation is identical to that of PLM60 and PLM85, but the size of liposomes was 100 nm.

Example 5

Preparation of Mitoxantrone Liposome PLM60-dppc

DPPC, cholesterol and DSPE-PEG2000 at a weight ratio of 3:1:1 were mixed, and other steps were identical to those of Example 2. The obtained liposomes were named as PLM60-dppc.

Example 6

Preparation of Mitoxantrone Liposome PLM60-dmpc

DMPC, cholesterol and DSPE-PEG2000 at a weight ratio of 3:1:1 were mixed, and other steps were identical to those of Example 2. The obtained liposomes were named as PLM60-dmpc.

Example 7

Preparation of Mitoxantrone Liposome PLM60-dmpc-0.1

DMPC, cholesterol and DSPE-PEG2000 at a weight ratio of 3:1:0.1 were mixed, and other steps were identical to those of Example 2. The obtained liposomes were named as PLM60-dmpc-0.1.

Example 8

Preparation of Adriamycin Liposome PLD60

Adriamycin was substituted for mitoxantrone during the step of loading drug, and other steps were identical to those of Example 2. The obtained liposomes were named as PLD60.

Part 2: Drug Release of Different Liposome Formulations

Example 9

Differences of Drug-Release Between Adriamycin Liposome PLD60 and Mitoxantrone Liposome PLM60

In the present example, mitoxantrone and adriamycin were loaded under a pH gradient. If a certain concentration of ammonium chloride was added to a release medium, free ammonia molecules would diffuse to the inner phase of liposome with the help of gradient, so that the pH of inner phase would be elevated and the protonated drug in the inner phase would be converted into its neutral form which could diffuse across membrane. This process could accelerate the dissolution of precipitation in the inner phase of liposome in the meantime. The speed of drug release was controlled by both the dissolution of precipitation and the membrane permeability of liposome. The conditions for drug release were as follows. Liposomes were diluted by 25 times with release media. The release media were isotonic, had a pH of 7.4, and had a concentration of ammonium chloride of 2, 10 and 40 mM, respectively. The diluted liposomes were placed in dialysis tubings, and dialysis was performed on 2 mL diluted liposome by 400 mL of release medium at 37° C. Samples were taken at different time points for analysis until 96 hours later.

The obtained data were subjected to an regression analysis. In the release media having 2, 10 and 40 mM ammonium chloride, the drug-release half-life periods of PLD60 were 94.3, 31.9 and 11.2 hours, respectively. With regard to PLM60, no obvious release was observed in the three release media. Since PLD60 and PLM60 have no difference in composition and size, the difference of drug release kinetic characteristic could be attributed to their different pharmaceutical features. Adriamycin and mitoxantrone are both anthracycline antibiotics, and their differences lie in that adriamycin contains one dissociable group at physiological pH while mitoxantrone contains two dissociable groups (pKa=8.15) at physiological pH. This example illustrates that a drug with multi-dissociable groups such as mitoxantrone can form a complex precipitation with counter-ions when an active loading method is employed, so that the in vitro release of drug is significantly slowed down. On the other hand, a drug with uni-dissociable group such as adriamycin could be released too quickly even in a release medium without plasma when a small size liposome is employed.

Example 10

Release Behaviors of Mitoxantrone Liposomes with Different Sizes

Two release conditions were taken to compare the release behaviors of mitoxantrone liposomes with different size.

Release condition 1: a liposome was diluted by 25 times with a release medium. The release medium contained 50% human plasma, was adjusted to be isotonic by glucose and had a pH of 7.4. Other conditions were identical to those of Example 9. The obtained data were subjected to a regression analysis. The result showed that the release half-life period of PLM60 was 56.4 hours, while PLM85 was not significantly released under the same conditions.

Release condition 2: a release medium containing 50% human plasma and 20 mM ammonium chloride was used, and other conditions were identical to those of Example 9. The obtained data were subjected to a regression analysis. The result showed that the release half-life period of PLM60 was 26.2 hours, while the release half-life period of PLM85 was 36.7 hours.

This example sufficiently indicated that the release of drug could be significantly enhanced by reducing the size of liposome.

Example 11

Release Behaviors of Mitoxantrone Liposomes with Different Membrane Compositions The same release conditions as described in Example 9 were used. The result indicated that the release half-life of PLM60-DPPC was 116 hours, the release half-life of PLM60-DMPC was 26 hours, and the release half-life of PLM60-DMPC-0.1 was 15 hours. This example indicated that the use of a phospholipid with a lower phase transition temperature Tm could accelerate the drug release. However, if the release of drug was accelerated excessively, the toxicity of drug could increase excessively as well, and this was further confirmed in the following examples.

Part 3: In Vivo Pharmacokinetics

Example 12

Pharmacokinetic Behavior of PLM60 in Kunming Mice and the Comparison Between PLM60 and Free Mitoxantrone This example was conducted in male Kunming mice with a body weight of about 20 g. Different dose levels of mitoxantrone were injected through tail vein in mice. The dosages of PLM60 were 1, 2 and 4 mg/kg, and the dosage of free mitoxantrone (FM) was 2 mg/kg. Plasma samples were taken at different time points. The methods for processing and detecting plasma samples were described in the document: Methods in enzymology, Vol: 391, p176-185. The results were shown in Table 1 and FIG. 1, in which it was clearly indicated that the half-life period of mitoxantrone was significantly extended by encapsulation of liposomes. At the same dosage, PLM60 had a retention time in blood circulation 32 times of that of FM, and an AUC 3700 times of that of FM. A plot of AUC against dose indicated that PLM60 had a linear pharmacokinetics in vivo.

TABLE 1

Pharmacokinetics of PLM60 and FM in Kunming mice

| Parameters | PLM60 4 mg/kg Value | PLM60 2 mg/kg Value | PLM60 1 mg/kg Value | FM 2 mg/kg Value |
|---|---|---|---|---|
| AUC 0-48(mg/L*h) | 1451.666 | 728.398 | 452.709 | 0.198 |
| AUC 0-∞(mg/L*h) | 1654.543 | 892.437 | 503.078 | 0.199 |
| AUMC 0-48 | 21838.034 | 12050.681 | 7049.259 | 0.103 |
| AUMC 0-∞ | 36234.611 | 24686.917 | 10488.811 | 0.135 |
| MRT 0-48(h) | 15.043 | 16.544 | 15.571 | 0.517 |
| MRT 0-∞(h) | 21.900 | 27.662 | 20.849 | 0.675 |
| $T_{max}$(h) | 0.083 | 0.083 | 0.250 | 0.083 |
| $C_{max}$(mg/L) | 86.329 | 47.513 | 25.970 | 0.699 |

Example 13

Tissue Distribution of PLM60 and FM in Tumor-Bearing Mice

Figure 2:
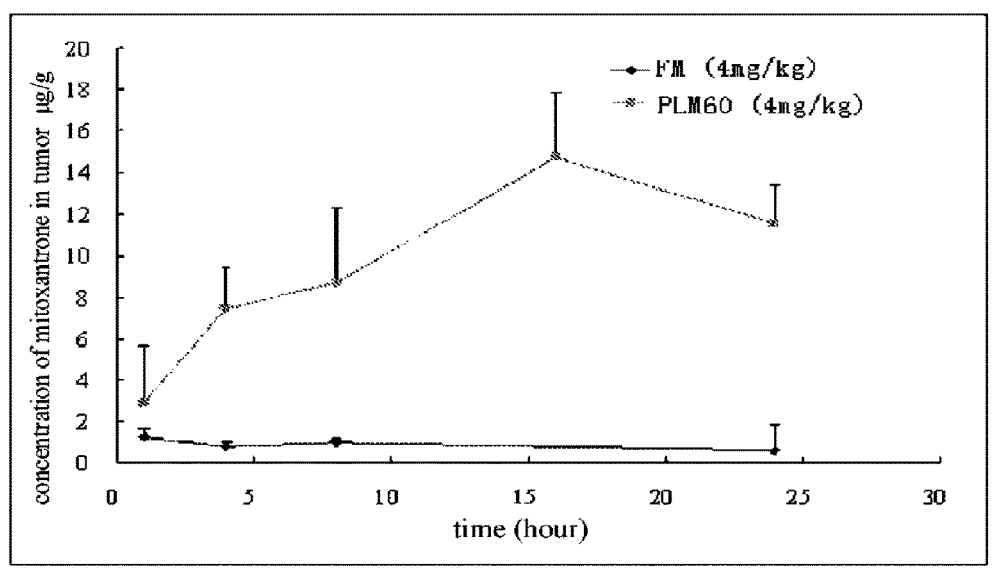
FIG. 2 is the profile of PLM60 and FM in mice tumor, in which PLM60 represents PEGylated mitoxantrone liposome, FM represents free mitoxantrone, the abscissa represents time (hour) and the ordinate represents the concentration of mitoxantrone in tumor tissues (μg mitoxantrone/g tumor tissue).

There were obvious differences in tissue distribution between PLM60 and FM in tumor-bearing mice. Male Kunming mice having a body weight about 20 g were used in the present example. The mice were inoculated in right oxter with S-180 sarcoma cells at a ration of 5×105. Drugs were injected through vein in mice when tumor grew to 0.4-0.7 g. After the administration of drugs, mice were executed at various time points and their tissues were taken out to determine the concentration of mitoxantrone. The tissues included hearts, livers, spleens, lungs, kidneys, intestines, bone marrow and tumors. The results showed that PLM60 had a very clear targeting to tumor tissues. The detailed data were shown in Table 2 and FIG. 2.

TABLE 2

Tissue distribution data of PLM60 and FM in tumor-bearing mice

| Tissue | PLM-60 4 mg/kg | | | FM 4 mg/kg | | |
|---|---|---|---|---|---|---|
| | t(h) | C-µg/g | SD | t(h) | C-µg/g | SD |
| Heart | 1 | 4.01 | 0.38 | 1 | 5.385 | 0.679 |
| | 4 | 3.39 | 0.38 | 4 | 3.517 | 0.952 |

TABLE 2-continued

Tissue distribution data of PLM60 and FM in tumor-bearing mice

| Tissue | PLM-60 4 mg/kg | | | FM 4 mg/kg | | |
|---|---|---|---|---|---|---|
| | t(h) | C-µg/g | SD | t(h) | C-µg/g | SD |
| | 8 | 3.48 | 0.64 | 8 | 3.197 | 0.357 |
| | 16 | 2.83 | 0.57 | 24 | 2.943 | 0.549 |
| | 24 | 2.06 | 0.48 | | | |
| Liver | 1 | 6.78 | 0.78 | 1 | 4.770 | 0.997 |
| | 4 | 5.99 | 0.67 | 4 | 3.556 | 0.543 |
| | 8 | 6.31 | 0.38 | 8 | 2.659 | 0.439 |
| | 16 | 6.22 | 0.95 | 24 | 1.937 | 0.346 |
| | 24 | 4.52 | 0.65 | | | |
| Spleen | 1 | 4.66 | 1.37 | 1 | 4.044 | 0.414 |
| | 4 | 4.36 | 0.67 | 4 | 4.460 | 0.494 |
| | 8 | 4.78 | 1.70 | 8 | 3.774 | 2.676 |
| | 16 | 7.56 | 2.13 | 24 | 7.752 | 2.469 |
| | 24 | 5.91 | 1.00 | | | |
| Lung | 1 | 8.44 | 1.08 | 1 | 10.205 | 1.732 |
| | 4 | 4.58 | 2.36 | 4 | 8.024 | 1.859 |
| | 8 | 6.33 | 1.43 | 8 | 7.018 | 0.728 |
| | 16 | 5.12 | 1.24 | 24 | 8.082 | 0.844 |
| | 24 | 2.89 | 0.23 | | | |
| Kidney | 1 | 7.09 | 0.84 | 1 | 18.243 | 1.238 |
| | 4 | 7.12 | 1.17 | 4 | 17.192 | 5.010 |
| | 8 | 7.04 | 0.96 | 8 | 13.409 | 1.251 |
| | 16 | 6.75 | 1.16 | 24 | 7.463 | 1.209 |
| | 24 | 5.82 | 0.84 | | | |
| Intestine | 1 | 1.66 | 0.66 | 1 | 1.532 | 0.309 |
| | 4 | 2.33 | 0.66 | 4 | 2.140 | 0.655 |
| | 8 | 2.34 | 0.64 | 8 | 2.551 | 1.204 |
| | 16 | 2.42 | 0.51 | 24 | 3.936 | 1.625 |
| | 24 | 2.25 | 0.32 | | | |
| Bone marrow | 1 | 1.09 | 0.54 | 1 | 0.127 | 0.041 |
| | 4 | 0.64 | 0.14 | | | |
| | 8 | 0.73 | 0.16 | | | |
| | 16 | 0.54 | 0.24 | | | |
| | 24 | 0.12 | 0.02 | | | |
| Tumor | 1 | 91.28 | 7.41 | 1 | 0.0614 | 0.0078 |
| | 4 | 63.90 | 8.56 | 4 | 0.0133 | 0.0027 |
| | 8 | 54.01 | 8.04 | | | |
| | 16 | 38.61 | 9.19 | | | |
| | 24 | 10.41 | 2.67 | | | |

Example 14

Pharmacokinetics Comparison of Different Liposome Formulations

Figure 3:
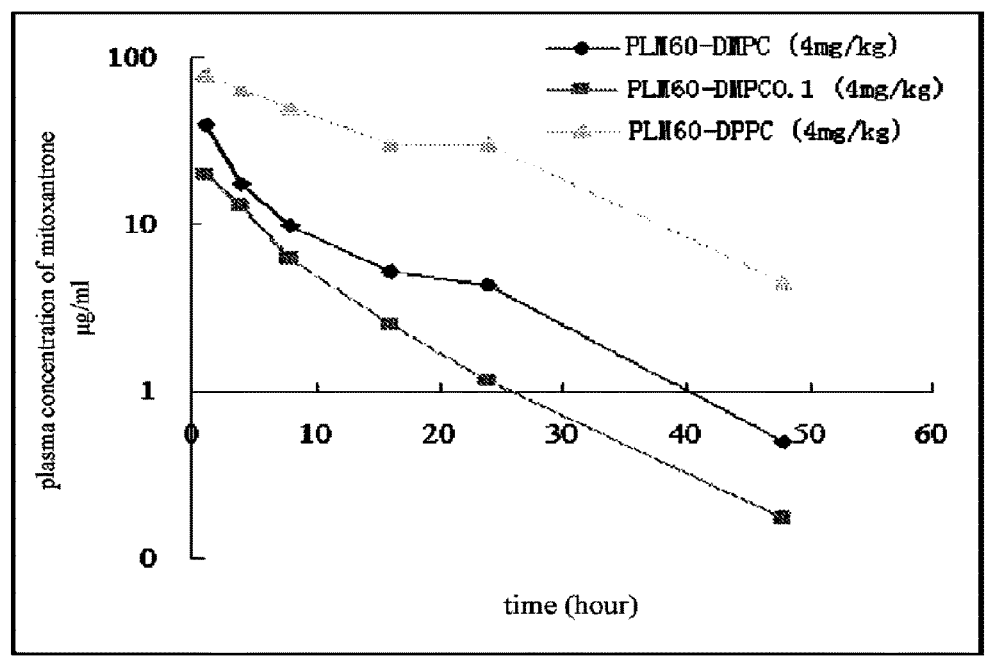
FIG. 3 is the comparison of in vivo pharmacokinetics in mice of different formulations, in which the abscissa represents time (hour) and ordinate represents the plasma level of mitoxantrone (μg mitoxantrone/mL plasma), and the dosages of different formulations are all 4 mg/kg.

The animals used in this example were similar to those of Example 12. PLM60-DPPC, PLM60-DMPC-0.1 and PLM60-DMPC at 4 mg/kg were injected through tail vein in mice. The data were shown in Table 3 and FIG. 3. It was shown that pharmacokinetics of liposomal drugs changed significantly with the change of liposome membrane composition. The MRT values of PLM60-DPPC, PLM60-DMPC-0.1 and PLM60-DMPC in vivo were 14.22, 7.914 and 10.123 hours, respectively. The difference between PLM60-DPPC and PLM60-DMPC lied in the lengths of hydrocarbon chains of phospholipids, which were 16 and 14 carbons, respectively. The length of acyl chain could significantly influence the membrane permeability of phospholipid bilayer. The phase transition temperature of DPPC was 41° C. and the phase transition temperature of DMPC was 23° C. The difference between PLM60-DMPC-0.1 and PLM60-DMPC lied in the degree of PEGylation. The release of liposomal drug in plasma depends on two factors: one is the release of liposomal drug across phospholipid bilayer and the other is the clearance by lipoprotein and reticuloendothelial system (RES). Since the PEGylation of PLM60-DMPC-0.1 was not complete, the release caused by plasma components had more influences on it.

TABLE 3

Comparison of in vivo pharmacokinetics of different liposome formulations in mice

| Parameter | PLM60-DPPC 4 mg/kg Value | PLM60-DMPC-0.1 4 mg/kg Value | PLM60-DMPC 4 mg/kg Value |
|---|---|---|---|
| AUC 0-48(mg/L*h) | 1506.710 | 174.849 | 337.641 |
| AUC 0-∞(mg/L*h) | 1581.242 | 175.705 | 344.134 |
| AUMC 0-48 | 21425.274 | 1383.757 | 3417.981 |
| AUMC 0-∞ | 26235.613 | 1478.267 | 3818.856 |
| MRT 0-48(h) | 14.220 | 7.914 | 10.123 |
| MRT 0-∞(h) | 16.592 | 8.413 | 11.097 |
| $T_{max}$(h) | 1.000 | 1.000 | 1.000 |
| $C_{max}$(mg/L) | 81.976 | 19.853 | 39.115 |

Part 4: Comparison of Toxicity of Different Formulations

Example 15

Comparison of Acute Toxicity Between PLM60 and FM

100 Kunming mice (half male and half female) with a body weight of 18-22 g were divided into 10 groups, each group had 10 mice, half male and half female. Mice of groups 1-5 were administrated with different dose levels of FM, while mice of groups 6-10 were administrated with an equivalent dose level of liposomal drug. Body weight changes were observed and the death time of each animal was recorded. The dead animals were dissected and autopsied. The results of all groups were shown in Table 4, which showed that the acute toxicity of PLM60 was far lower than that of FM.

TABLE 4

Acute toxicity comparison of PLM60 and FM to Kunming mice

| Liposome and dose | Survival time of male mice (day) | | | | | Survival time of female mice (day) | | | | |
|---|---|---|---|---|---|---|---|---|---|---|
| mg/kg | No. 1 | No. 2 | mg/kg | No. 1 | No. 2 | mg/kg | No. 1 | No. 2 | mg/kg | No. 1 |
| FM 20 | 7 | 8 | FM 20 | 7 | 8 | FM 20 | 7 | 8 | FM 20 | 7 |
| FM 12 | 18 | 13 | FM 12 | 18 | 13 | FM 12 | 18 | 13 | FM 12 | 18 |
| FM 7.2 | NA | NA | FM 7.2 | NA | NA | FM 7.2 | NA | NA | FM 7.2 | NA |
| FM 4.32 | NA | NA | FM 4.32 | NA | NA | FM 4.32 | NA | NA | FM 4.32 | NA |
| FM 2.59 | NA | NA | FM 2.59 | NA | NA | FM 2.59 | NA | NA | FM 2.59 | NA |

TABLE 4-continued

Acute toxicity comparison of PLM60 and FM to Kunming mice

| Liposome and dose | Survival time of male mice (day) | | | | | Survival time of female mice (day) | | | | |
|---|---|---|---|---|---|---|---|---|---|---|
| mg/kg | No. 1 | No. 2 | mg/kg | No. 1 | No. 2 | mg/kg | No. 1 | No. 2 | mg/kg | No. 1 |
| PLM60 20 | 17 | NA | PLM60 20 | 17 | NA | PLM60 20 | 17 | NA | PLM60 20 | 17 |
| PLM60 12 | NA | NA | PLM60 12 | NA | NA | PLM60 12 | NA | NA | PLM60 12 | NA |
| PLM60 7.2 | NA | NA | PLM60 7.2 | NA | NA | PLM60 7.2 | NA | NA | PLM60 7.2 | NA |
| PLM60 4.32 | NA | NA | PLM60 4.32 | NA | NA | PLM60 4.32 | NA | NA | PLM60 4.32 | NA |
| Liposome and dose | Survival time of male mice (day) | Survival time of female mice (day) | Liposome and dose | Survival time of male mice (day) | Survival time of female mice (day) | Liposome and dose | Survival time of male mice (day) | Survival time of female mice (day) | Liposome and dose | Survival time of male mice (day) |

NA: No data, i.e., No animal died at the end of experimental observation.

Example 16

Acute Toxicity Comparison of Different Liposome Formulations 90 male Balb/c mice with a body weight of 18-22 g were divided into 9 groups, each group had 10 mice. The mice of group 1 were administered with FM at 6 mg/kg, while mice of other 8 groups were administered with PLM60, PLM60-DPPC and PLM60-DMPC-0.1 and PLM60-DMPC at 6 and 12 mg/kg, respectively. Body weight changes were observed and the death time of each animal was recorded. The dead animals were dissected and autopsied. The results of death of mice of FM group and liposomal drug groups were shown in Table 5. This experiment showed that the order of acute toxicity was: PLM60<PLM60-DPPC<PLM60-DMPC-0.1 FM<PLM60-DMPC. This experiment also confirmed that the release of drug could be further accelerated by using small unilamellar vesicles and phospholipid with a lower Tm as the composition of bilayer, such as PLM60-DMPC, thereby resulting in more toxicity in vivo. It should be noted that the toxicity of liposomes with incomplete PEGylation was lower than that of liposomes with more complete PEGylation. This may be attributed to that under the action of lipoprotein and the attack of immune system during blood circulation, PLM60-DMPC-0.1 with incomplete PEGylation would release drug earlier in comparison with PLM60-DMPC and would not release suddenly in important tissues, thereby exhibiting a lower toxicity, but the toxicity of PLM60-DMPC-0.1 was still nearly equivalent to that of free mitoxantrone.

Example 17

Toxicity Comparison of Liposome Formulations with Different Sizes

Male C57 mice with a body weight of 18-22 g were used in toxicity comparison of PLM60, PLM85 and PLM100. The dose was 9 mg/kg. The results indicated that body weight varieties caused by the three liposome formulations were equivalent, which confirmed that the three liposome formulations had no significant difference in toxicity under the experimental conditions. In mice of FM group, the body weight decreased over 30% and about 20% mice died.

Part 5: In Vivo Anti-Tumor Effects

Example 18

Comparison of Treatment Effects of PLM60 and FM on S-180 Sarcoma

Ascitic tumor-bearing mice which were inoculated with S180 tumor cells 7 days ago were executed by decollation, and milky viscous ascitic fluid was extracted and diluted with RPMI 1640 medium. After dilution, the tumor cell number was adjusted to 2.5×106 cells/ml. 0.2 mL of the tumor cell suspension containing about 5×105 tumor cells was inoculated into forward limb oxter tissues of male KM mice with a body weight of 18-22 g. After inoculation, the

TABLE 5

Acute toxicity comparison of different liposomes

| | Survival time of mice(day) | | | | | | | | | |
|---|---|---|---|---|---|---|---|---|---|---|
| Formulary and dose(mg/kg) | 1 | 2 | 3 | 4 | 5 | 6 | 7 | 8 | 9 | 10 |
| FM-6 | NA | NA | NA | NA | NA | NA | NA | NA | NA | NA |
| PLM60-6 | NA | NA | NA | NA | NA | NA | NA | NA | NA | NA |
| PLM60-12 | NA | NA | NA | NA | NA | 10 | NA | NA | NA | 11 |
| Plm60DPPC-6 | NA | NA | NA | NA | NA | NA | NA | NA | NA | NA |
| Plm60DPPC-12 | 10 | 10 | 12 | 11 | NA | NA | NA | 13 | NA | 14 |
| Plm60-DMPC-6 | 4 | NA | NA | 3 | 6 | 7 | 7 | 6 | NA | NA |
| Plm60DMPC-12 | 3 | 3 | 5 | 3 | 3 | 3 | 4 | 3 | 3 | 3 |
| Plm60DMPC-0.1-6 | NA | NA | NA | NA | NA | NA | NA | NA | NA | NA |
| Plm60DMPC-0.1-12 | 10 | 12 | 10 | 12 | 10 | 10 | 10 | 11 | 10 | 10 |

NA: No animal died at the end of experimental observation cells in the residual tumor cell suspension were counted under light microscope, and living tumor cells were greater than 95%. The number of inoculated mice was 80.

Seven days after inoculation, 39 mice with clear-cut tumors having a diameter of about 5 mm were selected and divided into 5 groups by both tumor volume and body weight, i.e., 7 mice in blank control group, 8 mice in each of 4 mg/kg PLM60 group, 6 mg/kg PLM60 group, 4 mg/kg FM group and 6 mg/kg FM group. The mice were administered by intravenous injection.

The mice were bred normally after administration. Tumor diameters were measured by vernier caliper 3 times per week, and body weights were measured at the same time. Tumor volume (TV) was calculated with the following formula: $V=\frac{1}{2} \times a \times b^2$, in which a and b represent length and width, respectively. The tumor volumes were calculated by using the measurement results. Mice were executed by decollation on the 21st day after inoculation, tumors were taken out and weighed. Tumor inhibition rate (%) was calculated with the following formula: tumor inhibition rate=(1−average tumor weight of drug group/average tumor weight of control group)×100%. The experimental result was tested by t-test.

Table 6 showed that the growth of S180 solid tumor was significantly suppressed in the 4 mg/kg PLM60 group and 6 mg/kg PLM60 group.

TABLE 6

Effects of PLM60 on S180 solid tumor weight

| Group | Weight of tumor (mg) | Ratio of tumor-inhibiting (%) |
|---|---|---|
| Control | 2813.8 ± 884.2 | — |
| PLM60 4 mg/kg | 421.9 ± 215.4[a] | 85.00 |
| PLM60 6 mg/kg | 332.4 ± 162.5[a] | 88.19 |
| free mitoxantone 4 mg/kg | 2828.5 ± 1067.8 | — |
| free mitoxantone 6 mg/kg | 2293.3 ± 1720.0 | 18.50 |

[a]in comparison with the control group, $p < 0.01$

Example 19

Treatment Effects of PLM60 and FM on L1210 Ascites Model

Ascitic tumor BDF1 mice which were inoculated with L1210 ascitic tumor cells 7 days ago were executed by decollation, and milky viscous ascitic fluid was extracted under aseptic condition and diluted by RPMI 1640 medium. After dilution, the tumor cell number was adjusted to $2.5 \times 10^6$ cells/ml. 0.2 mL of the tumor cell suspension containing about $5.0 \times 10^5$ tumor cells was inoculated into the abdominal cavity of a 7-8 week-old female BDF1 mouse. After inoculation, the cells in the residual tumor cell suspension were counted under light microscope, and living tumor cells were greater than 95%.

24 hours later, the mice were divided into 8 groups by body weight, and were administered with FM at 2, 4 and 8 mg/kg, and PLM60 at 2, 4, and 6 mg/kg by injection in a volume of 20 ml/kg through tail vein in mice, respectively. After administration, the mice were bred normally. Their body weights were measured 3 times per week, the death time of each mouse was observed and recorded, and survival time was calculated. Mean survival time (MST) and median survival time were employed to evaluate the survival time of each group. Experimental observation was kept for 60 days after the inoculation.

The data were analyzed by SPSS 11.5 statistics software. The results showed that all administration groups exhibited significant increase of survival time in comparison with the control group, and the PLM60 (8 mg/kg) group exhibited significant improvement of treatment in comparison with the FM group at the same dose (P<0.05). The results were shown in Table 7.

TABLE 7

Effects of L1210 ascitic tumor on BDF1 mice survival time

| Group | Dose (mg/kg) | Number of animals (N) | Number of dead animals (N) | Mean survival time | Median survival time (95% confidence interval) | Ratio of survival (%) |
|---|---|---|---|---|---|---|
| Control | — | 13 | 13 | 9.62 ± 0.40 (8.83-10.40) | 9.00 ± 0.25 (8.51-9.49) | 0 |
| PLM60 | 2 | 12 | 11 | 20.17 ± 3.77 (12.77-27.56) | 14.00 ± 1.15 (11.74-16.26) | 8.33 |
|  | 4 | 12 | 9 | 36.75 ± 4.00 (28.92-44.58) | 31.00 ± 0.85 (29.33-32.67) | 25.00 |
|  | 6 | 12 | 10 | 28.42 ± 4.49 (19.63-37.21) | 25.00 ± 3.46 (18.21-31.79) | 16.67 |
| PLM60 | 2 | 12 | 9 | 36.42 ± 4.08 (28.41-44.42) | 29.00 ± 1.71 (25.65-32.35) | 25.00 |
|  | 4 | 11 | 2 | 57.55 ± 1.60 (54.40-60.69) | N[b] | 81.82 |
|  | 6 | 12 | 5 | 48.00 ± 4.38 (39.42-56.58) | N[b] | 58.33 |
|  | 8 | 12 | 4 | 53.00 ± 3.71 (45.72-60.28) | N[b] | 66.67 |

N[b]: Only few animals died at the end of experimental observation of 60 days and the median survival time could not be calculated.

Example 20

Treatment Effects of PLM60 and FM on L1210 Liver Metastasis Model

Ascitic tumor BDF1 mice which were inoculated L1210 ascitic tumor cells 7 days ago were executed by decollation, and milky viscous ascitic fluid was extracted under aseptic condition and diluted with RPMI 1640 medium. After dilution, the tumor cell number was adjusted to $2.5 \times 10^5$ cells/ml. 0.2 mL of the tumor cell suspension containing about $5.0 \times 10^4$ tumor cells was intravenously inoculated into a 7-8 week-old male BDF1 mouse. After inoculation, the cells in the residual tumor cell suspension were counted under light microscope, and living tumor cells were greater than 95%. Total 62 mice were inoculated.

24 hours later, the mice were grouped and administered. After administration, the mice were bred normally. The body weights of mice were measured 3 times per week, the death time of each mouse was observed and recorded every day, and survival time was calculated. Experimental observation was kept for 60 days after the inoculation.

The result showed that all mice in the control group died between the 11th and 14th day after inoculation, all mice in the three FM dose level groups died between the 11th and 17th day after inoculation, all mice in the 2 mg/kg PLM60 group died between the 15th and 29th day after inoculation, only one mouse in the 6 mg/kg PLM60 group died on the 39th day after inoculation, and no mouse in the 8 mg/kg PLM60 group died during the observation.

The data were analyzed by SPSS 11.5 statistics software. The results showed that the 6 mg/kg FM group and all liposomal drug groups exhibited a significant increase in survival time of mice in comparison with the blank control group. At same dose level, liposomal mitoxantrone exhibited a significant increase in survival time of mice in comparison with free mitoxantrone. The results were shown in Table 8.

TABLE 8

Effects of intravenous inoculation of L1210 on BDF1 mice survival time

| Group | Dose (mg/kg) | Number of animals (N) | Number of dead animals (N) | Mean survival time | Median survival time (95% confidence interval) | Survival rate (%) |
|---|---|---|---|---|---|---|
| Control | — | 6 | 6 | 11.83 ± 0.48 (10.90-12.77) | 11.0 | 0 |
| PLM60 | 2 | 8 | 8 | 12.13 ± 0.61 (10.93-13.32) | 11.0 | 0 |
| | 4 | 8 | 8 | 13.25 ± 0.53 (12.22-14.28) | 13.00 ± 0.46 (12.11-13.89) | 0 |
| | 6 | 8 | 8 | 14.50 ± 0.71 (13.11-15.89) | 14.00 ± 0.91 (12.21-15.79) | 0 |
| PLM60 | 2 | 8 | 8 | 19.13 ± 1.57 (16.04-22.21) | 18.00 ± 1.41 (15.23-20.77) | 0 |
| | 4 | 8 | 5 | 36.50 ± 6.51 (23.75-49.25) | 22.00 ± 5.660.61 (10.91-33.09) | 37.50 |
| | 6 | 8 | 1 | 57.38 ± 2.46 (52.56-62.19) | N[b] | 87.50 |
| | 8 | 8 | 0 | N[a] | N[a] | 100.00 |

N[a]: No animal died until at the end of 60 days experimental observation and the median survival time was not calculated.
N[b]: Only one of animals died at the end of 60 days experimental observation and the median survival time was not calculated.

Example 21

Treatment Effects of Liposomal Mitoxantrone with Different Size on L1210 Ascitic Tumor The experimental scheme and data process mode were the same as Example 19. Five groups were setup, including control group, FM group, PLM60 group, PLM85 group and PLM100 group. The administration dosage for mice in each group was 4 mg/kg. The results were shown in Table 9. The results showed that liposome with smaller size had better treatment effects.

TABLE 9

Effects of L1210 ascitic tumor on BDF1 mice survival time

| Group | Dose (mg/kg) | Number of animal (N) | Number of dead animal (N) | Mean survival time | Median survival time (95% confidence interval) | Survival rate (%) |
|---|---|---|---|---|---|---|
| Control | — | 12 | 12 | 9.08 ± 0.19 | 9.00 ± 0.21 | 0 |
| FM | 4 | 12 | 8 | 38.67 ± 3.54 | 36.00 ± 6.06 | 33.33 |

TABLE 9-continued

Effects of L1210 ascitic tumor on BDF1 mice survival time

| Group | Dose (mg/kg) | Number of animal (N) | Number of dead animal (N) | Survival time (95% confidence interval) | | Survival rate (%) |
|---|---|---|---|---|---|---|
| | | | | Mean survival time | Median survival time | |
| PLM60 | 4 | 12 | 4 | 47.00 ± 2.88 | $N^b$ | 66.67 |
| PLM85 | 4 | 12 | 8 | 39.17 ± 4.1 | 38.00 ± 11.26 | 33.33 |
| PLM100 | 4 | 12 | 10 | 30.08 ± 3.59 | 23.00 ± 2.89 | 16.66 |

$N^b$: Only few animals died at the end of 60 days experimental observation and the median survival time was not calculated Some preferred examples of the present invention are described above, but these examples are in no way intended to limit the scope of the invention. Besides what have been described and illustrated in the text, a skilled ordinary technician in the field would clearly realize other modifications and variations and changes of the present invention after reading the disclosure of the present invention, and all of them should be covered in the protection scope of the present invention. All patents, published patent applications and publications cited here are incorporated by reference, just like their full texts are incorporated in the text.

What is claimed:

1. A method for treating sarcoma, comprising administering to a patient in need thereof liposomes, wherein
   the liposomes encapsulate mitoxantrone, and have a mean size of 35-75 nm,
   the bilayer of the liposomes comprises (a) a phospholipid that is hydrogenated soybean phosphatidylcholine (HSPC), (b) cholesterol, and (c) PEG-modified distearoyl phosphatidyl ethaolamine (DSPE), and the intraliposomal phase of the liposomes comprises a multivalent counter ion,
   the phospholipid of (a) amounts to 55-95 mol/mol % relative to the total content of phospholipids of the liposomes,
   the cholesterol of (b) amounts to 2-60 mol/mol % relative to the mole number of the total amount of ingredients of the liposomes, and
   the PEG-modified DSPE of (c) amounts to 0.1-20 mol/mol % relative to the mole number of the total content of phospholipids of the liposomes.

2. The method of claim 1, wherein the phospholipid bilayer of the liposomes comprises additional phospholipid having a phase transition temperature (Tm) not higher than body temperature.

3. The method of claim 2, wherein the additional phospholipid comprises dimyristoyl phosphatidylcholine (DMPC).

4. The method of claim 1, wherein the PEG-modified DSPE amounts to 1-10 mol/mol % relative to the mole number of the phospholipid.

5. The method of claim 1, wherein the PEG-modified DSPE amounts to 2.5-7 mol/mol % relative to the mole umber of the phospholipid.

6. The method of claim 1, wherein the liposomes have a mean size of 40-75 nm.

7. The method of claim 1, wherein the liposomes have a mean size of 40-70 nm.

8. The method of claim 1, wherein the liposomes have a mean size of 40-60 nm.

9. The method of claim 1, wherein the liposomes comprise HSPC, cholesterol and PEG-modified distearoyl phosphatidyl ethanolamine in a weight ratio of 3:1:1.

10. The method of claim 9, wherein the PEG-modified distearoyl phosphatidyl ethanolamine is a PEG2000-modified distearolyl phosphatidyl ethanolamine.

11. The method of claim 1, wherein the liposomes comprise one or more additional active pharmaceutical ingredients, and/or pharmaceutically acceptable carriers and/or excipients.

12. The method of claim 1, wherein the multivalent counter ion is an organic acid anion, an inorganic acid anion, or an ionic from of amino acid.

13. The method of claim 12, wherein the organic acid anion is an acid anion of citric acid, tartaric acid, fumaric acid, oxalic acid, malonic acid, succinic acid, malic acid, or maleic acid; the inorganic acid anion is sulfate anion or phosphate anion; and an ionic form of amino acid is cysteine.

* * * * *